US011484439B2

(12) United States Patent
Sinha et al.

(10) Patent No.: US 11,484,439 B2
(45) Date of Patent: Nov. 1, 2022

(54) INFECTION CONTROL SYSTEM FOR FORCED AIR WARMING MACHINES

(71) Applicant: Care Essentials Pty Ltd, Victoria (AU)

(72) Inventors: Abhay Sinha, Victoria (AU); Ishan Sinha, Victoria (AU)

(73) Assignee: Care Essentials Pty Ltd, Victoria (AU)

( * ) Notice: Subject to any disclaimer, the term of this patent is extended or adjusted under 35 U.S.C. 154(b) by 600 days.

(21) Appl. No.: 16/606,878

(22) PCT Filed: Apr. 27, 2018

(86) PCT No.: PCT/AU2018/050394
§ 371 (c)(1),
(2) Date: Oct. 21, 2019

(87) PCT Pub. No.: WO2018/201186
PCT Pub. Date: Nov. 8, 2018

(65) Prior Publication Data
US 2020/0129325 A1     Apr. 30, 2020

(30) Foreign Application Priority Data

May 2, 2017     (AU) ................................ 2017901599

(51) Int. Cl.
| *A61F 7/00* | (2006.01) |
| *A61B 46/10* | (2016.01) |
| *A61B 50/30* | (2016.01) |
| *C08L 23/12* | (2006.01) |
| *A61B 50/00* | (2016.01) |

(52) U.S. Cl.
CPC ............ *A61F 7/0085* (2013.01); *A61B 46/10* (2016.02); *A61B 50/30* (2016.02); *C08L 23/12* (2013.01); *A61B 2050/005* (2016.02); *A61F 2007/006* (2013.01)

(58) Field of Classification Search
CPC .. A61F 7/0085; A61F 2007/006; A61B 46/10; A61B 46/00; C08L 23/12
See application file for complete search history.

(56) References Cited

U.S. PATENT DOCUMENTS

| 4,934,152 | A | 6/1990 | Templeton |
| 9,504,601 | B1 | 11/2016 | Lewis |
| 2011/0017213 | A1 | 1/2011 | Vadney |
| 2016/0256314 | A9 | 9/2016 | Loushin |

OTHER PUBLICATIONS

Albrecht, M., et al., "Forced-air warming blowers: An evaluation of filtration adequacy and airborne contamination emissions in the operating room," American Journal of Infection Control, vol. 39, No. 4, pp. 321-328, May 2011.

*Primary Examiner* — Jonathan T Kuo
(74) *Attorney, Agent, or Firm* — Rahman LLC

(57) ABSTRACT

A single-use infection control system for a forced air warming machine having hosing connected to the machine including: a closable container having a chamber to receive the machine, the container constructed from air permeable material that prevents infectious airborne particles from entering the chamber; a sleeve having a first end and a second end, the first end engaged to an aperture on the container and the sleeve surrounding the hosing; and a filter cap constructed from the air permeable material, disposed at the second end and covering an opening of the hosing.

20 Claims, 7 Drawing Sheets

INFECTION CONTROL SYSTEM FOR FORCED AIR WARMING MACHINES

FIELD OF THE INVENTION

The present invention relates to an infection control system for forced air warming machines used in medical theatres.

BACKGROUND OF THE INVENTION

Conventionally, forced air warming machines that are currently available and used in conjunction with forced air warming blankets in medical practice is that they are all multi-use warming machines. That is, the forced air warming machines and its associated connected air hosing are used on many patients for the commercial life of the forced air warming machine. Although the warming blankets are single use blankets, the forced air machine and associated air hosing are multi-use devices.

Forced air warming machines operate by drawing cool air into the machine externally from the machine, then passing through an internal filter and warmed air is forced out of the machine and through the associated air hosing which is connected to the forced air warming blankets.

One problem arises from the use of the forced air warming machine is that infectious airborne pathogens including viruses, bacteria and fungi from the present patient, is deposited airborne onto the internal air filter, and air grill/fins of the forced air warming machine and on the inside of the associated air hosing.

Another problem arises from the use of the forced air warming machine and its associated air hosing, is that other infectious pathogens including viruses, bacteria and fungi from the present patient can be transmitted by physical human contact on the outside of the forced air warming machine itself and on the outside of the associated air hosing.

Further, these internal filters of the forced air warming machines are not changed after each single use on each patient, and are certainly not changed at the end of each day of conducting medical and clinical procedures.

Depending upon the commercial brand of these forced air warming machines, these associated internal air filters are changed every 500-1000 hours of continuous medical use.

Therefore, as a consequence of the above medical practise of using the forced air warming machines, infectious pathogens including viruses, bacteria and fungi, accumulate and colonize in and on the forced air warming machine itself, as well as depositing infectious pathogens on the internal air filter of the forced air warming machine and inside the connected associating air hosing, spreading cross infections, from patient to patient, resulting from such further multi-use.

It therefore an object of the present invention to provide for an infection control system for multi-use forced air warming machines and associated hosing in order to ameliorate all of the above problems.

SUMMARY OF INVENTION

Accordingly, in one aspect, the present invention provides a single-use infection control system for a forced air warming machine having hosing connected to the machine including:

a closable container having a chamber to receive the machine, the container constructed from air permeable material that prevents infectious airborne particles from entering the chamber;

a sleeve having a first end and a second end, the first end engaged to an aperture on the container and the sleeve surrounding the hosing; and a filter cap constructed from the air permeable material, disposed at the second end and covering an opening of the hosing.

In another aspect, the present invention provides a single-use infection control system for a forced air warming machine having hosing connected to the machine including:

a closable container having a chamber to receive the machine, the container constructed from air permeable material that prevents infectious airborne particles from entering the chamber; and a sleeve constructed from the air permeable material and having a first end and a second end, the first end engaged to an aperture on the container, the sleeve surrounding the hosing and the second end covering an opening of the hosing.

Preferably, the container includes a transparent window.

Preferably, the transparent window is constructed from material including biaxially orientated polypropylene film Preferably, the container includes a lid to cover the transparent window.

Preferably, the lid is sealable to the transparent window.

One advantage of the single-use infection control system for a forced air warming machine is that infectious airborne pathogens including viruses, bacteria and fungi from one patient are not deposited on the internal air filter, and air grill/fins of the forced air warming machine and on the inside of the connected air hosing, thereby reducing cross infection with another patient that uses the same forced air warming machine.

Another advantage of the single-use infection control system for a forced air warming machine is that infectious pathogens including viruses, bacteria and fungi from one patient are prevented from physically contacting the outside of the forced air warming machine and connected air hosing thereby reducing cross infection with another patient that uses the same forced air warming machine.

It will be convenient to hereinafter to describe the invention with reference to the following drawings which shows seven (7) preferred embodiments of the single-use infection control system for a forced air warming machine according to the invention. The particularity of the attached drawings and following description should not supersede or limit the preceding broad definition of the invention.

DETAILED DESCRIPTION OF THE INVENTION

Figure 1:
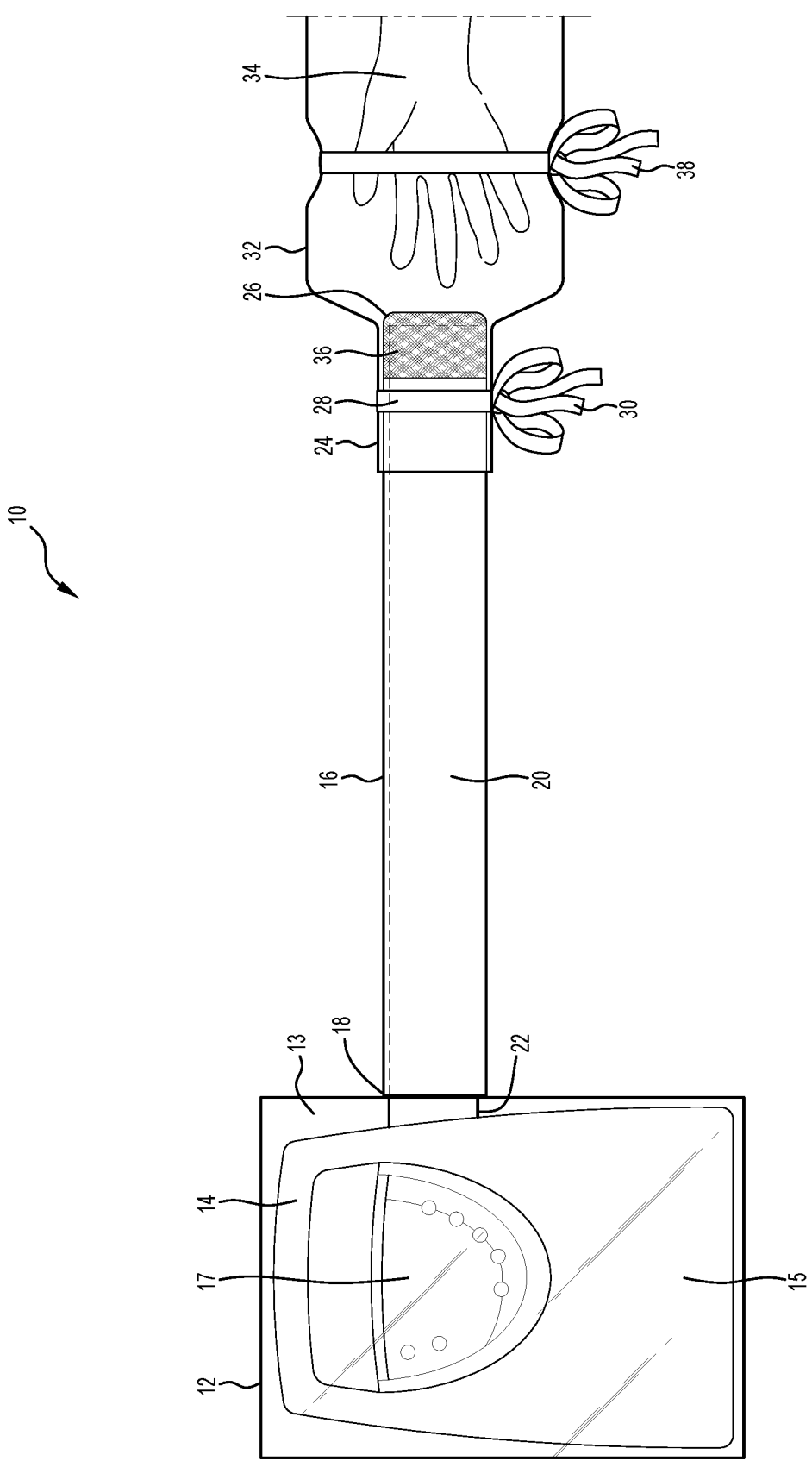
FIG. 1 is a cross sectional (in part) perspective view of the single-use infection control system for a forced air warming machine according to a first preferred embodiment of the invention, illustrating the single-use infection control system in use in conjunction with a blanket for forced air warming and a hand of a patient.

FIG. 1 illustrates the cross sectional (in part) perspective view of the single-use infection control system for a forced air warming machine 10 illustrating the closable container 12 having a chamber 13 which functions to receive the forced air warming machine 14 and enclose the entire forced air warming machine 14 from the external air environment. In this FIG. 1, the sleeve 16 is engaged by way of connection 18 being a join or integral forming with the closable container 12 to an aperture (not illustrated) on the closable container 12 that provides the air communication access to the chamber 13. The hosing 20 of the forced air warming machine 14 is enclosed or surrounded by the sleeve 16 for its entire length and the sleeve 16 extends to a filter cap 26. The person skilled in the art will appreciate that the hosing 22 extends to the hosing 36 which has an opening (not illustrated) for air communication channel purposes exiting warm air forced air from the forced air warming machine 14. The hosing 22 extends back toward and is connected to the forced air warming machine 14. The person skilled in the art will also appreciate that the filter cap 26 covers the opening (not illustrated) of the hosing 36. The hosing 20 and hosing 36 is covered by the sleeve 16. The sleeve 16 at one end, extends back and is connected to closable container 12 to the aperture (not illustrated) and at the other end, the sleeve 16 is disposed or movably engaged to the filter cap 26.

The closable container 12 on its front, includes a transparent window 15 constructed from material including biaxially orientated polypropylene film. The transparent window 15 functions to allow the medical practitioner or nurse to operate the forced air warming machine 14 by using the transparent window 15 as a touch pad and visually observe and operate a machine console 17 displayed on the forced air warming machine 14.

In use, the single-use infection control system for a forced air warming machine 10 is assembled by placing a blanket for forced air warming 24 at the other end of the sleeve 16 being where the hosing 36 and filter cap 26 are both located. The filter cap 26 covers the opening (not illustrated) of the hosing 36 as previously described. A machine tie 28 and machine tie 30 secure the blanket for forced air warming 24 over the filter cap 26 and sleeve 16 at the hosing 36 end. A patient's hand 34 is previously positioned under the blanket for forced air warming 32 that is secured by a patient tie 38. The blanket for forced air warming 32 receives the forced warm air from the forced air warming machine 14 through the hosing 22, hosing 20 and hosing 36. By operating the machine console 17 through the transparent window 15, the forced air warming machine 14 functions to draw air external to the closable container 12 and through the chamber 13 and draw air inside the forced air warming machine 14 and pass through its internal filter (not illustrated but being a Bacteriological HEPA Filter of 0.2 micron), which then heats the drawn and filtered air up to a 36° C. to 37.5° C. and then is forced out by positive air pressure through its connected hosing 22, hosing 20 and hosing 36.

The closable container 12 is constructed from air permeable material that prevents infectious airborne particles from entering the chamber 13 external to the closable container 12. The Infectious airborne particles include bacteria, viruses and fungi. The unique feature is the air permeable material is constructed from spun bond, melt-blown, spun bond (sms) non-woven polypropylene; spun bond, melt-blown, melt-blown, spun bond (smms) non-woven polypropylene; spun bond, melt-blown, melt-blown, melt blown, spun bond (smmms) non-woven polypropylene; spun bond, spun bond, melt-blown, melt-blown, spun bond (ssmms) non-woven polypropylene; and a combination of any one or more of the foregoing. When the forced air warming machine 14 functions to draw air external to the closable container 12 and through the chamber 13 and draw air inside the forced air warming machine 14, the air is filtered by the closable container 12 such that it prevents infectious airborne particles from entering the chamber 13 and therefore the forced air warming machine 14. The air, first entering the forced air warming machine 14 from the chamber 13 through the closable container 14 is first filtered. When the first filtered air enters the forced air warming machine 14, it is further filtered by the internal air filter within the forced air warming machine 14 which is described herein.

The sleeve 16 is also constructed from the air permeable material including: spun bond, melt-blown, spun bond (sms) non-woven polypropylene; spun bond, melt-blown, melt-blown, spun bond (smms) non-woven polypropylene; spun bond, melt-blown, melt-blown, melt blown, spun bond (smmms) non-woven polypropylene; spun bond, spun bond, melt-blown, melt-blown, spun bond (ssmms) non-woven polypropylene; and a combination of any one or more of the foregoing.

In an alternative embodiment, the sleeve 16 may also be constructed from non-air permeable material including polyvinyl chloride, biaxially orientated polypropylene film and any non-woven fabric material coated with polyethylene, which also acts as a physical barrier for both infectious airborne particles and infectious non-airborne particles that spread by physical contact.

The filter cap 26 is constructed from the same air permeable material, as the closable container 12 as described herein. When the double filtered forced warm air described above exits the forced air warming machine 14, and entered the hosing 22 and hosing 20, the forced warm air is advantageously further filtered by the filter cap 26 at the opening of the hosing 36 to be triple filtered for infectious airborne particles including bacteria, fungi and viruses, before the forced warm air enters the blanket for forced air warming 24.

Figure 2:
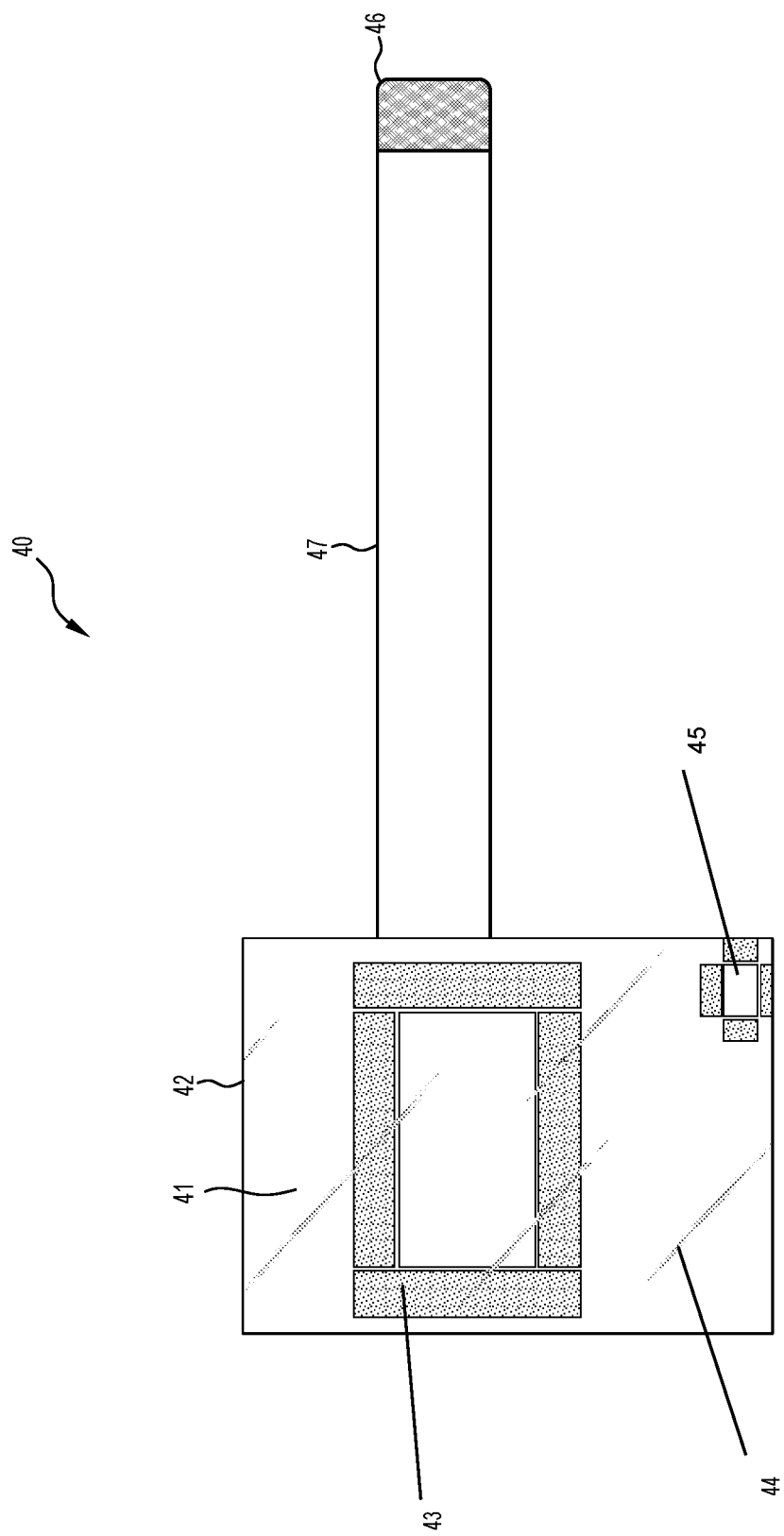
FIG. 2, is a front perspective view of the single-use infection control system for a forced air warming machine according to a second preferred embodiment of the invention, illustrating the system in an assembled but unused state on a patient and with no forced air warming machine inside the closable container.

Turning to FIG. 2, is a front perspective view of the single-use infection control system for a forced air warming machine 40 in an assembled but unused state on a patient. A closable container 42 constructed from the air permeable materials described above, is engaged or connected to a sleeve 47 by way a join or integral forming by the aperture (not illustrated) presented on the closable container 42, that provides air communication access to a chamber 41. A filter cap 46 constructed from the same air permeable materials described above is disposed at one end of the sleeve 47. The filter cap 46 can be separately secured to the sleeve 47 by way of interconnection including a slide fit over the sleeve 47, snug fit under the sleeve 47 or alternatively secured to the sleeve 47, by way of moveable engagement to the sleeve 47. The person skilled in the art will appreciate that the single-use infection control system for a forced air warming machine 40 is of a unitary construction. The closable container 42 also has a second aperture 43 located on the rear wall of the closable container 42, which functions to provide access to the rear of the forced air warming machine (not illustrated) to anchor the forced air warming machine (not illustrated) to a fixed or moveable IV Pole of a patient when in use. The person skilled in the art will appreciate that that the second aperture 43 is identifiable from FIG. 2 because of the transparent window 44 located at the front of the closable container 42. Further, the person skilled in the art will also appreciate that when the forced air warming machine (not illustrated) is positioned inside the chamber 41, the second aperture 43 does not necessarily provide air communication access to the chamber 41. The closable container 42 also has a third aperture 45 located on the rear wall of the closable container 42 to provide access to a power source such as a power cord to supply the forced air warming machine (not illustrated). Similarly, the person skilled in the art will also appreciate that when the forced air warming machine (not illustrated) is positioned inside the chamber 41, the third aperture 45 does not necessarily provide air communication access to the chamber 41.

Figure 3:
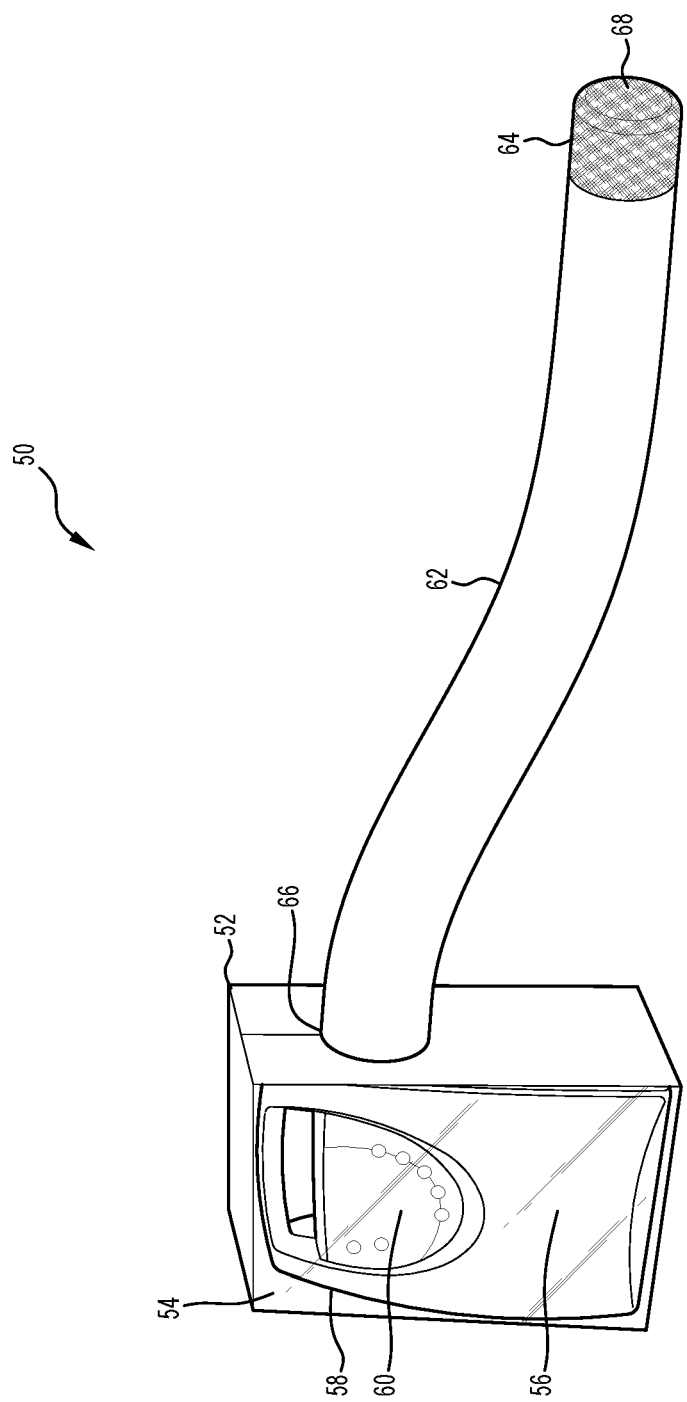
FIG. 3 is an alternative perspective view of the single-use infection control system for a forced air warming machine of FIG. 1, according to a third preferred embodiment of the invention, illustrating the closable container and a connected sleeve and filter cap (the latter of which in partial cross-section), with no blanket for forced air warming assembled.

Now turning to FIG. 3, is an alternative perspective view of the single-use infection control system for a forced air warming machine 50 having a forced air warming machine 58 presenting its machine console 60 and illustrating a closable container 52 and its chamber 54 through the transparent window 56. A sleeve 62 at one end, is connected or joined to the closable container 52 by a connection 66 surrounding an aperture (not illustrated) presented on the side of the closable container 52. The connection 66 is either fixed or integrally formed. The sleeve 62 surrounds the hosing (not illustrated) which in turn, is internally connected to the forced air warming machine 58. The sleeve 62 at the other end is engaged by interconnection to a filter cap 64 by way of slide fit of the filter cap 64 over the sleeve 62, snug fit of the filter cap 64 under the sleeve 62 or moveable connection to the sleeve 62 such that the filter cap 64 covers an opening 68 of the hosing (not illustrated as a whole) that provides the advantageous and unique further filter function of the forced warm air passing through the hosing (not illustrated as a whole) before entering a forced air warming blanket, which is not illustrated or assembled in this FIG. 3. The person skilled in the art will appreciate that the user of the forced air warming machine 58 can hand operate the machine console 60 through the transparent window 56 by touch pad means.

Figure 4:
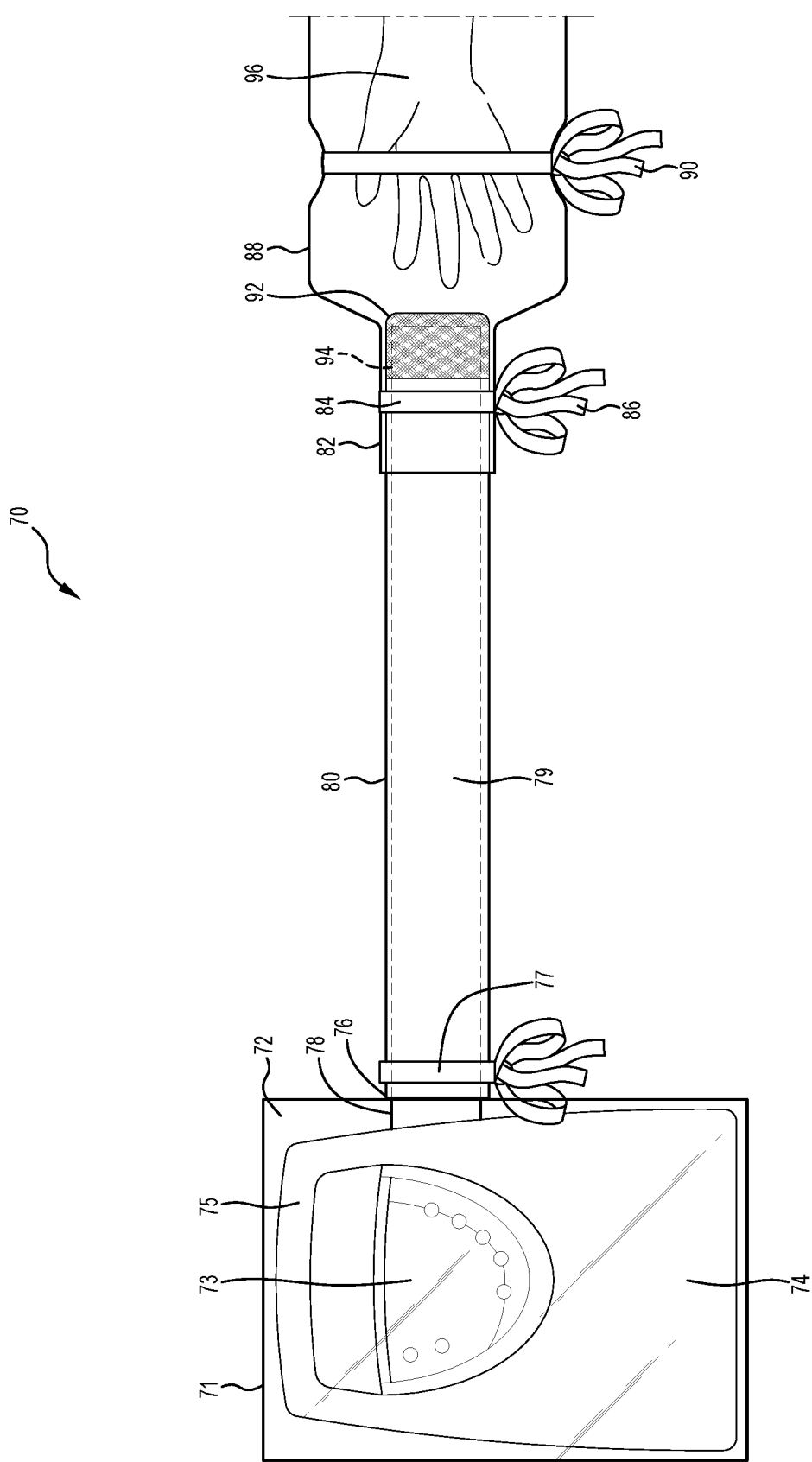
FIG. 4 is a cross sectional (in part) perspective view of an alternative embodiment of a single-use infection control system for a forced air warming machine according to a fourth preferred embodiment of the invention, illustrating the single-use infection control system in use in conjunction with a blanket for forced air warming and a hand of a patient.

Now turning to FIG. 4, is a cross sectional (in part) perspective view of an alternative embodiment of a single-use infection control system for a forced air warming machine 70, illustrating the system in use in conjunction with a blanket for forced air warming 82 and a patient's hand 96, having a forced air warming machine 75 presenting its machine console 73 and illustrating a closable container 71 and its chamber 72 through the transparent window 74. A sleeve 80 at one end, engages the closable container 71 by way of an interconnection 76, whereby the sleeve 80 engages or meets the aperture (not illustrated), presented on the side of the closable container 71. The interconnection 76 is different to FIG. 1 as the sleeve 80 engages the aperture (not illustrated) by slide fit and is not fixed, nor permanently connected to the closable container 71. The sleeve 80 is secured to the hosing 79 by a machine tie 77. The sleeve 80 is a separate part to the closable container 71. The sleeve 80 surrounds the hosing 79, which in turn, extends back and is internally connected to the forced air warming machine 75. The sleeve 80 at the other end is engaged to a filter cap 92 by way of interconnection, by way of slide fit of the filter cap 92 over the sleeve 80 or snug fit of the filter cap 92 under the sleeve 80. Alternatively, the filter cap 92 is moveably connected to the sleeve 80 such that the filter cap 92 covers an opening (not illustrated) of the hosing 94 that provides a further filter function of the forced warm air passing through the hosing 94, before entering a blanket for forced air warming 88. The person skilled in the art will appreciate that the user of the forced air warming machine 75 can hand operate the machine console 73 through the transparent window 74 by touch pad using the hand operator's fingers.

The closable container 71 on its front, includes a transparent window 74 constructed from material including biaxially orientated polypropylene film. The transparent window 74 functions to allow the medical practitioner or nurse to operate the forced air warming machine 75 by using the transparent window 74 as a touch pad and visually observe and operate the machine console 73 on the forced air warming machine 75.

The closable container 71 and filter cap 92 are both constructed from the same air permeable filter material that filters airborne infectious particles including bacteria, viruses and fungi described above. The sleeve 80 is also constructed from the same air permeable filter material that filters airborne infectious described above. Alternatively, the sleeve 80 is constructed from non-air permeable material including polyvinyl chloride, biaxially orientated polypropylene film and any non-woven fabric material coated with polyethylene, which also acts as a physical barrier for both infectious airborne particles and infectious non-airborne particles that spread by physical contact.

In use, the single-use infection control system for a forced air warming machine 70 is assembled by placing a blanket for forced air warming 82 over and at one end of the sleeve 80 and surrounding the sleeve 80 where the hosing 94 and filter cap 92 are both located. The filter cap 92 covers the opening (not illustrated) of the hosing 94 as previously described. A machine tie 84 and machine tie 86 secures the blanket for forced air warming 82 over the filter cap 92 and sleeve 80 at the hosing 94 end.

A patient's hand 96 is previously positioned under the blanket for forced air warming 88 and secured by the patient tie 90 that receives the forced warm air from the forced air warming machine 75 through the hosing 78 and hosing 79 and through the secured and interconnected blanket for forced air warming 88. By operating the machine console 73 through the transparent window 74, the forced air warming machine 75 functions to draw air outside the closable container 71 and into the chamber 72 and prevent infectious airborne particles from entering the chamber 72 and draw air inside the forced air warming machine 75 and pass through its internal filter (not illustrated) and then heated up to a 36° C. to 37.5° C. The double filtered heated air is then forced out by positive air pressure through its connected hosing 78, hosing 79 and exiting out of the hosing 94, passing through the filter cap 92 to be advantageously and uniquely triple filtered to prevent infectious airborne particles spreading, before the forced warm air enters the blanket for forced air warming 88.

The person skilled in the art will also appreciate that FIG. 4 is illustrative of a preferred embodiment being the single-use infection control system for a forced air warming machine 70 in use in conjunction with a blanket for forced air warming 88 being a hand blanket (not illustrated fully in FIG. 4). Other types of blankets for forced air warming can be used in conjunction with the single-use infection control system for a forced air warming machine 70 and it is not limited to a hand blanket and includes a full-bodied blanket, a lower bodied blanket and an upper body arms-in blanket.

In an alternative embodiment not illustrated in FIG. 1 to FIG. 4, a mounting flange or mounting rim is inserted inside the opening of the blanket for forced air warming 82 to maintain the opening, which in turn provides the necessary engagement or interconnection for the hosing 94 and filter cap 92 to insert therethrough. The machine tie 84 and machine tie 86 secures the blanket for forced air warming 82 over the filter cap 92 and sleeve 80 at the hosing 94 end.

Figure 5:
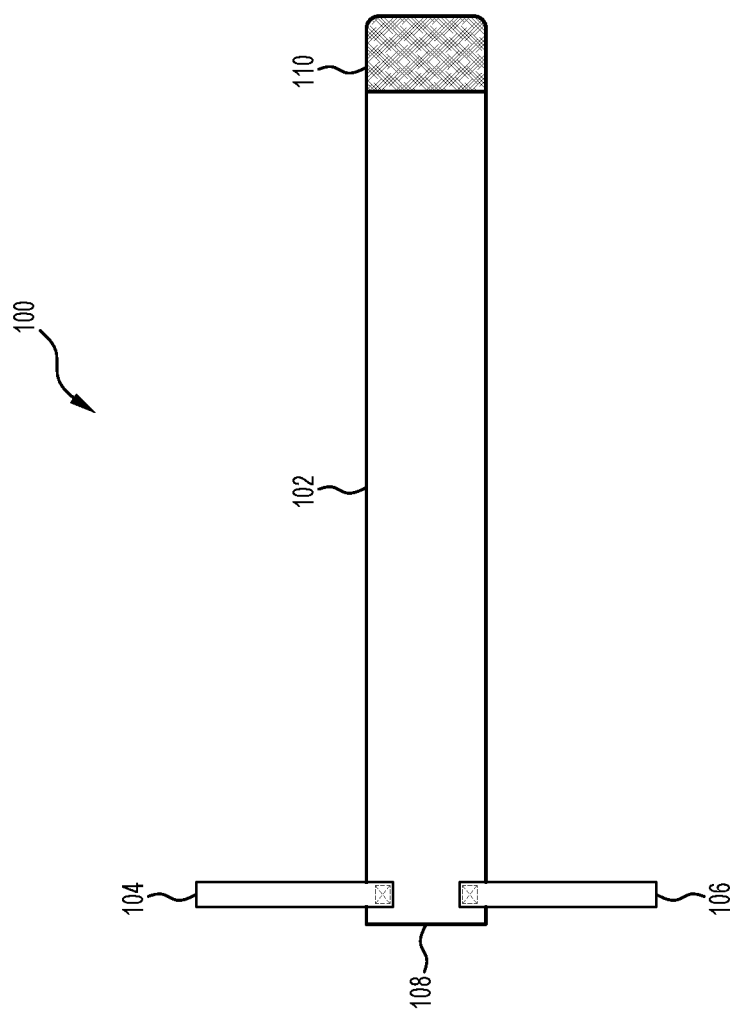
FIG. 5 is a perspective view of a interconnectable sleeve and filter cap of the single-use infection control system for a forced air warming machine of FIG. 4, according to a fifth preferred embodiment of the invention.

Now turning to FIG. 5 is a perspective view of a interconnectable sleeve and filter cap 100 of the single-use infection control system for a forced air warming machine of FIG. 4, having a sleeve 102 that surrounds the hosing (not illustrated) of a forced air warming machine (also not illustrated). At one end the sleeve 102 a machine tie 104 and machine tie 106 secures the sleeve 102 to the hosing (not illustrated) of the forced air warming machine (not illustrated). At this first end, the sleeve 102 has an opening 108 for channel purposes that surrounds the hosing (not illustrated). At the other end of the sleeve 102, a filter cap 110 constructed from the air permeable materials described above. The filter cap 110 is separately secured to the sleeve 102 by way of interconnection including a slide fit, snug fit or alternatively secured to the sleeve 102, by way of moveable engagement to the sleeve 102.

In an alternative embodiment and not illustrated in FIG. 5, the separate interconnectable sleeve and filter cap 100 is of unitary construction. That is, the sleeve 102 extends as one unitary integer with a closed end but air permeable providing the necessary filtration function of preventing infectious airborne particles from passing through the sleeve 102 from an opening of the hosing (not illustrated) connected to the forced air warming machine. The first end of the sleeve 102 is engaged to the aperture (not illustrated) in the closable container (not illustrated in FIG. 5) and the second or other end of the sleeve 102 covers an opening of the hosing.

Figure 6:
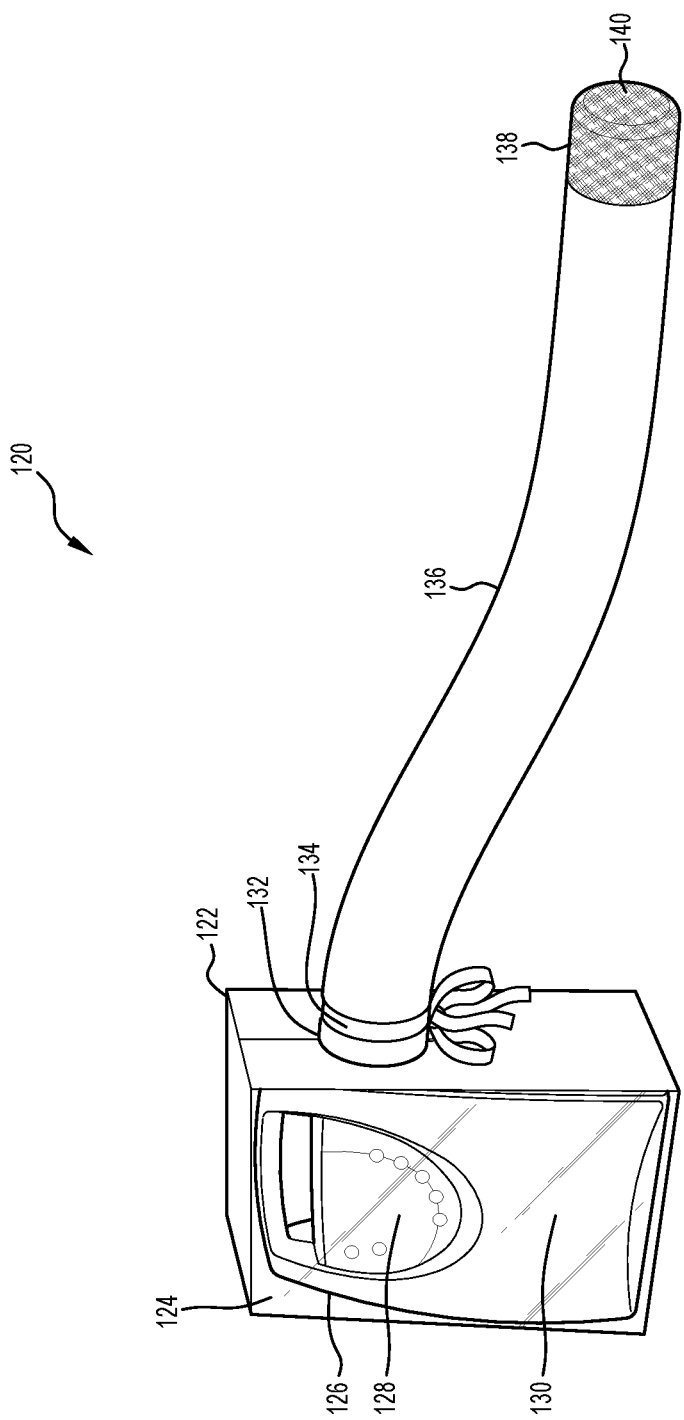
FIG. 6 is the single-use infection control system for a forced air warming machine of FIG. 4, according to a sixth preferred embodiment of the invention illustrating the closable container and an interconnected sleeve and filter cap (the latter of which in partial cross-section)

Now turning to FIG. 6, the single-use infection control system for a forced air warming machine 120 having a forced air warming machine 126 presenting its machine console 128 and illustrating a closable container 122 and its chamber 124 inside and which is visible through the transparent window 130. A sleeve 136 at one end is engaged to the closable container 122 by an interconnection 132 involving the sleeve 136 entering an aperture (not illustrated) presented on the side of the closable container 122 and is secured by use of a machine tie 134. The sleeve 136 surrounds the hosing (not illustrated) which in turn, is internally connected to the forced air warming machine 126. The sleeve 136 at its other end is engaged to a filter cap 138 by way of slide fit interconnection or moveable connection to the sleeve 136 such that the filter cap 138 (as illustrated in partial cross section in this FIG. 6) covers an opening 140 of the hosing (not illustrated) that advantageously provides a further filter function of the forced warm air passing through the hosing (not illustrated as a whole) before entering a forced air warming blanket, which is not illustrated or assembled in this FIG. 6. The person skilled in the art will appreciate that the user of the forced air warming machine 126 can operate the machine console 128 through the transparent window 130.

Figure 7:
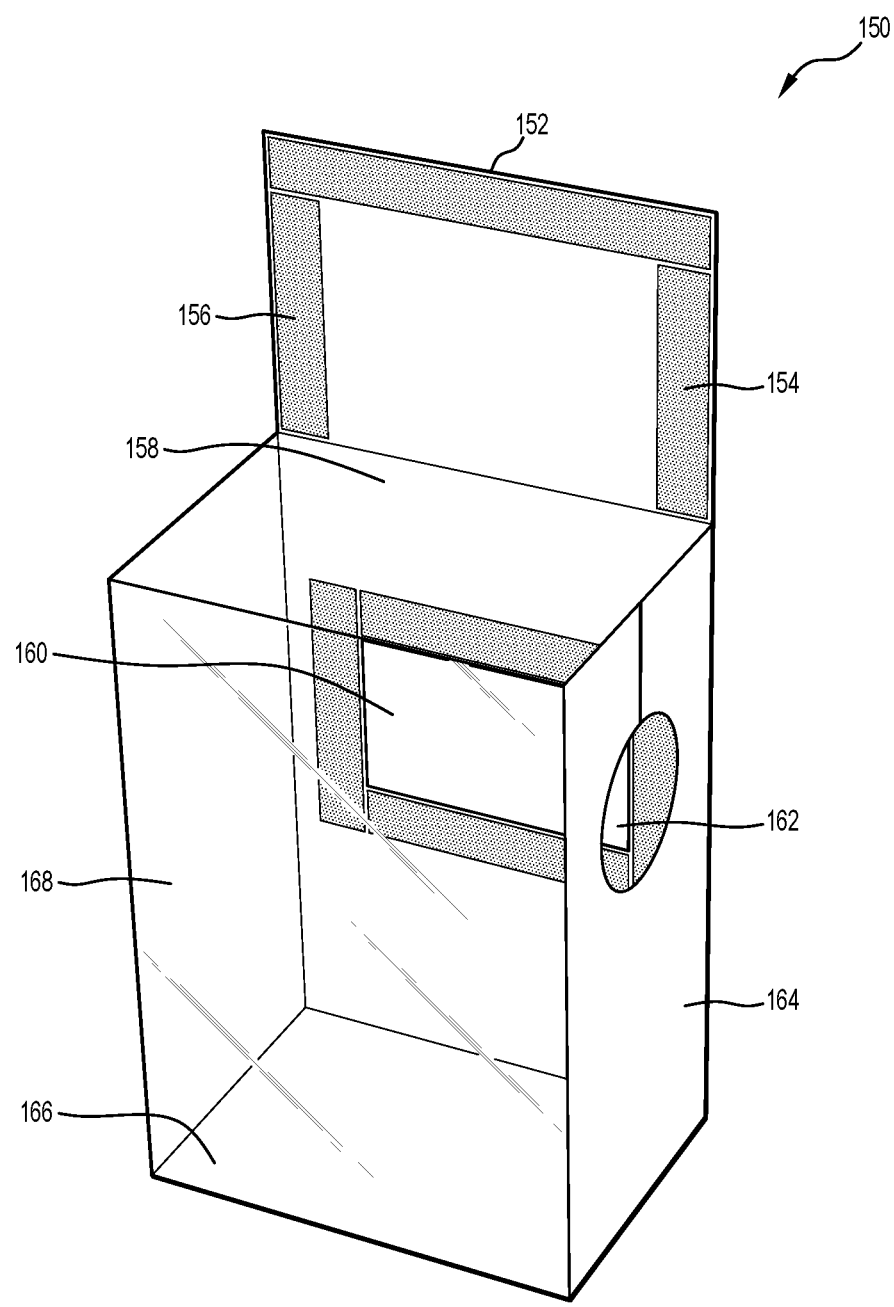
FIG. 7 is the single-use infection control system for a forced air warming machine of FIG. 4, according to a seventh preferred embodiment of the invention illustrating a front perspective view of the closable container with no assembled interconnectable sleeve and filter cap.

Now finally turning to FIG. 7 is the single-use infection control system for a forced air warming machine of FIG. 4, illustrating a front perspective view of the closable container 150 with no assembled interconnectable sleeve and filter cap or alternatively, no interconnectable sleeve as a unitary construction being illustrated. The closable container 150 has a base 166 and side wall 164. The side wall 164 presents a first aperture 162 that provides air communication access to the chamber 158 disposed inside the closable container 150, which is visually exposed by the transparent window 168 on its front position to receive the forced air warming machine (not illustrated). A second aperture 160 at the rear of the closable container 150 provides access to the rear of the forced air warming machine (not illustrated) to anchor the forced air warming machine to a fixed or moveable IV Pole of a patient when in use. A lid 152 is movable and functions not only to close the closable container 150, the lid 152 substantially covers the transparent window 168, given the dimensions and shape of the forced air warming machine, which is described below. The lid 152 is presented with sealing means 154 and sealing means 156 sealable to the transparent window 168 by way of any appropriate medical grade means such as Velcro™ or medical grade adhesive tape. The person skilled in the art will appreciate that the dimensions of the lid 152 are such that it will extend and substantially cover the entire transparent window 168 when in a closed position.

The closable container 150 also has a third aperture (not illustrated) positioned towards the base and rear of the closable container at the right-hand corner side near the base 166 (when inspecting FIG. 7) to access a power source such as a power cord to supply the forced air warming machine. The forced air warming machine is commercially available by Care Essentials Pty Ltd known as "Cocoon™ CWS 4000 *Therapeutic Goods Act* (Cth) Medical Device & MDD 93/42/ECC Class IIb device).

It is best to use the single-use infection control system for a forced air warming machine 10 and 70 the first time the forced air warming machine 14 of FIG. 1 (for example) is ever used, to ensure that the internal filter of the forced air warming machine 14 and associated hosing is not contaminated by any patient's bacteria, viruses or fungi. This means that the forced warm air is advantageously and always triple air filtered from infectious airborne particles, when entering the blanket for forced air warming 24 of FIG. 1 and 82 of FIG. 4.

The use the single-use infection control system for a forced air warming machine 10 and 70 is a single use system. That is, once used on one patient after a medical procedure, the single-use infection control system for a forced air warming machine 10 and 70 is then removed off the forced air warming machine 14 (of FIG. 1) to be fitted with another single-use infection control system for a forced air warming machine to be used on a subsequent patient.

The single-use infection control system for a forced air warming machine 10 and 70 is sterilized for infection control and used in a sterile form. The single-use infection control system for a forced air warming machine 10 and 70 can be sterilized before it is packaged for medical use and/or after it is placed into its package for subsequent medical use. Any suitable form of sterilization method in the art may be used.

One advantage of the single-use infection control system for a forced air warming machine is that infectious airborne pathogens including viruses, bacteria and fungi from one patient are not deposited onto the internal air filter, and air grill/fins of the forced air warming machine and on the inside of the connected air hosing, thereby reducing cross infection with another patient that uses the same forced air warming machine.

Another advantage of the single-use infection control system for a forced air warming machine is that infectious pathogens including viruses, bacteria and fungi from one patient are prevented from physically contacting the outside of the forced air warming machine and connected air hosing thereby reducing cross infection with another patient that uses the same forced air warming machine.

Various alterations and/or additions may be made to the single-use infection control system for a forced air warming machine hereinbefore described in this Specification, without departing from the spirit, ambit or scope of the invention.

A reference to any prior art in this Specification is not, and should not be taken as, an acknowledgment or any form or suggestion that the prior art forms part of the common general knowledge.

The invention claimed is:

1. A single-use infection control system for a forced air warming machine having hosing connected to the machine including:
    a closable container having a chamber to receive the machine, the container constructed from air permeable material that prevents infectious airborne particles from entering the chamber;
    a sleeve having a first end and a second end, the first end engaged to an aperture on the container and the sleeve surrounding the hosing; and
    a filter cap constructed from the air permeable material, disposed at the second end and covering an opening of the hosing.

2. The single-use infection control system according to claim 1, wherein the container includes a transparent window.

3. The single-use infection control system according to claim 2, wherein the transparent window is constructed from material including biaxially orientated polypropylene film.

4. The single-use infection control system according to claim 2, wherein the container includes a lid to cover the transparent window.

5. The single-use infection control system according to claim 4, wherein the lid is sealable to the transparent window.

6. The single-use infection control system according to claim 5, wherein the lid is sealable by way of Velcro™ or adhesive tape.

7. The single-use infection control system according to claim 1, wherein the aperture provides air communication access to the chamber.

8. The single-use infection control system according to claim 1, wherein the container includes a further aperture to access a power source.

9. The single-use infection control system according to claim 1, wherein the sleeve is secured or interconnected to the container.

10. The single-use infection control system according to claim 1, wherein the filter cap is secured or interconnected to the sleeve.

11. The single-use infection control system according to claim 1, wherein the filter cap is moveably engageable to the sleeve.

12. The single-use infection control system according to claim 1, wherein the air permeable material is constructed from: spun bond, melt-blown, spun bond (sms) non-woven polypropylene; spun bond, melt-blown, melt-blown, spun bond (smms) non-woven polypropylene; spun bond, melt-blown, melt-blown, melt blown, spun bond (smmms) non-woven polypropylene; spun bond, spun bond, melt-blown, melt-blown, spun bond (ssmms) non-woven polypropylene; and a combination of any one or more of the foregoing.

13. The single-use infection control system according to claim 1, wherein the sleeve is constructed from material including: polyvinyl chloride; biaxially orientated polypropylene film; non-woven fabric material coated with polyethylene; spun bond, melt-blown, spun bond (sms) non-woven polypropylene; spun bond, melt-blown, melt-blown, spun bond (smms) non-woven polypropylene; spun bond, melt-blown, melt-blown, melt blown, spun bond (smmms) non-woven polypropylene; spun bond, spun bond, melt-blown, melt-blown, spun bond (ssmms) non-woven polypropylene; and a combination of any one or more of the foregoing.

14. The single-use infection control system according to claim 1, wherein the infectious airborne particles include bacteria, viruses and fungi.

15. A single-use infection control system for a forced air warming machine having hosing connected to the machine including:
    a closable container having a chamber to receive the machine, the container constructed from air permeable material that prevents infectious airborne particles from entering the chamber; and
    a sleeve constructed from the air permeable material and having a first end and a second end, the first end engaged to an aperture on the container, the sleeve surrounding the hosing and the second end covering an opening of the hosing.

16. The single-use infection control system according to claim 15, wherein the container includes a transparent window.

17. The single-use infection control system according to claim 16, wherein the transparent window is constructed from material including biaxially orientated polypropylene film.

18. The single-use infection control system according to claim 15, wherein the container includes a lid to cover the transparent window.

19. The single-use infection control system according to claim 18, wherein the lid is sealable to the transparent window.

20. The single-use infection control system according to claim 15, wherein the container includes a further aperture to access a power source.

* * * * *